(12) United States Patent
Maruyama

(10) Patent No.: US 8,241,207 B2
(45) Date of Patent: Aug. 14, 2012

(54) CONNECTION MECHANISM OF PLATE MEMBER AND SHAFT MEMBER

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 1098 days.

(21) Appl. No.: 12/137,739

(22) Filed: Jun. 12, 2008

(65) Prior Publication Data

US 2008/0319264 A1 Dec. 25, 2008

(30) Foreign Application Priority Data

Jun. 21, 2007 (JP) ................................. 2007-163337

(51) Int. Cl.
*A61B 1/00* (2006.01)

(52) U.S. Cl. ........................................ 600/148; 600/102

(58) Field of Classification Search .................. 600/102, 600/146, 148
See application file for complete search history.

(56) References Cited

U.S. PATENT DOCUMENTS

| | | | | |
|---|---|---|---|---|
| 3,750,865 | A | * | 8/1973 | Harrell ........................... 198/722 |
| 4,207,873 | A | * | 6/1980 | Kruy ............................. 600/146 |
| 5,393,165 | A | * | 2/1995 | Rowan, Jr. .................... 403/301 |
| 5,501,408 | A | * | 3/1996 | Kang et al. ................. 242/356.5 |
| 5,507,717 | A | | 4/1996 | Kura et al. |
| 2005/0137453 | A1 | | 6/2005 | Ouchi et al. |
| 2005/0197532 | A1 | | 9/2005 | Sasaki et al. |
| 2006/0088303 | A1 | | 4/2006 | Ito |
| 2007/0010713 | A1 | | 1/2007 | Negishi |
| 2007/0255104 | A1 | | 11/2007 | Maruyama |
| 2008/0114377 | A1 | | 5/2008 | Shibata et al. |

FOREIGN PATENT DOCUMENTS

| | | |
|---|---|---|
| JP | 7-194519 | 8/1995 |
| JP | 9-98942 | 4/1997 |
| JP | 10-286220 | 10/1998 |
| JP | 11-47082 | 2/1999 |
| JP | 2003-135384 | 5/2003 |
| JP | 2007-313292 | 12/2007 |

OTHER PUBLICATIONS

English language Abstract of JP 7-194519, Aug 1, 1995.
English language Abstract of JP 9-98942, Apr. 15, 1997.
English language Abstract of JP 10-286220, Oct. 27, 1998.
English language Abstract of JP 11-47082, Feb. 23, 1999.
English language Abstract of JP 2003-135384, May 13, 2003.
English language Abstract of JP 2007-313292, Dec. 6, 2007.
U.S. Appl. No. 12/137,770 to Maruyama, which was filed Jun. 12, 2008.
U.S. Appl. No. 12/137,755 to Maruyama, which was filed Jun. 12, 2008.

* cited by examiner

*Primary Examiner* — Anhtuan Nguyen
*Assistant Examiner* — Alireza Nia
(74) *Attorney, Agent, or Firm* — Greenblum & Bernstein, P.L.C.

(57) ABSTRACT

A connection mechanism is provided with a plate member formed with a polygonal hole, the plate member including a first plate and a second plate overlaid with each other, each of the first plate and the second plate being formed with the polygonal hole, a shaft member formed with a polygonal column section fitted in the polygonal hole formed on the plate member, and a fixing mechanism that fixes the first plate and the second plate with each other to retain a status where the first plate and the second plate are urged oppositely in a rotational direction about a central axis of the shaft member.

3 Claims, 7 Drawing Sheets

CONNECTION MECHANISM OF PLATE MEMBER AND SHAFT MEMBER

BACKGROUND OF THE INVENTION

The following descriptions relate to a connection mechanism for connecting a plate member and a shaft member employed, for example, in an endoscope.

Generally, at an operation section of an endoscope, connection mechanisms such as a mechanism for operating a bending portion of an insertion section of the endoscope, a mechanism for changing an rising angle of a treatment tool and the like are provided. Such a mechanism employs a connection mechanism which connects the plate member with the shaft member such that the plate member does not rotate relative to the shaft member.

Typically, in such a connection mechanism, a portion of the shaft member is formed to have a shape of a polygonal column, and a polygonal opening to be engaged with the polygonal column portion is formed on the plate member. By fitting the polygonal column portion into the polygonal opening, the plate member and the shaft member do not rotate with respect to each other. An example of such a configuration is disclosed in Japanese Patent Provisional Publication No. HEI 9-98942.

When the above structure is employed, due to manufacturing errors, there may be some play between the plate member and the shaft member in the rotational direction. If an endoscope having such a problem is shipped as a product, an operator of the endoscope may not operate the endoscope (e.g., the operator may not control the degree of bend of the bendable section as intended).

FIG. 9 shows a conventional connection mechanism to deal with the above problem, and FIG. 10 is a cross section taken along line X-X in FIG. 9. In FIGS. 9 and 10, 92 denotes the plate member, and 91 denotes the shaft member. According to this example, screw holes 93 which extend substantially in a radial direction with respect to a central axis 91$ax$ of the shaft member 91 are formed on the plate member 92. The shaft member has a polygonal column section 91$x$ which is inserted in a polygonal opening 92$x$. Then, by inserting screws 94 through the screw holes 93 and fastening the same, tip ends of the screws 94 press-contact the polygonal column section 91$x$ in the radial directions, respectively, thereby play between the plate member 92 and shaft member 91 can be prevented.

In order to prevent the play between the plate member 92 and the shaft member 91 effectively, however, as shown in FIG. 10, at least three screws 94 should be used to push the polygonal column section 91$x$ in different directions. That is, if only a single screw 94 is used, the plate member may incline with respect to a plane perpendicular to the central axis 91$ax$ of the shaft member 91. Since the three screws 94 should be employed, assembling work of the structure shown FIGS. 9 and 10 is inefficient. Further, in the structure shown in FIGS. 9 and 10, the screws 94 may be loosened relatively easily, and after elapse of a relatively short period, play may occur between the plate member 92 and shaft member 91.

SUMMARY OF THE INVENTION

The present invention is advantageous in that an improved connection mechanism for connecting the shaft member formed with the polygonal section and the plate member formed with a corresponding polygonal opening without play therebetween with a relatively simple structure.

According to an aspect of the invention, there is provided a connection mechanism, which is provided with a plate member formed with a polygonal hole, the plate member including a first plate and a second plate overlaid with each other, each of the first plate and the second plate being formed with the polygonal hole, a shaft member formed with a polygonal column section fitted in the polygonal hole formed on the plate member, and a fixing mechanism that fixes the first plate and the second plate with each other to retain a status where the first plate and the second plate are urged oppositely in a rotational direction about a central axis of the shaft member.

Since the first plate and the second plate are urged oppositely in the rotational direction, the polygonal section of the shaft is kept tightly fitted in the polygonal hole.

BRIEF DESCRIPTION OF THE ACCOMPANYING DRAWINGS

DETAILED DESCRIPTION OF THE EMBODIMENTS

Hereinafter, referring to the accompanying drawings, connection mechanisms according to embodiments of the invention will be described.

Figure 2:
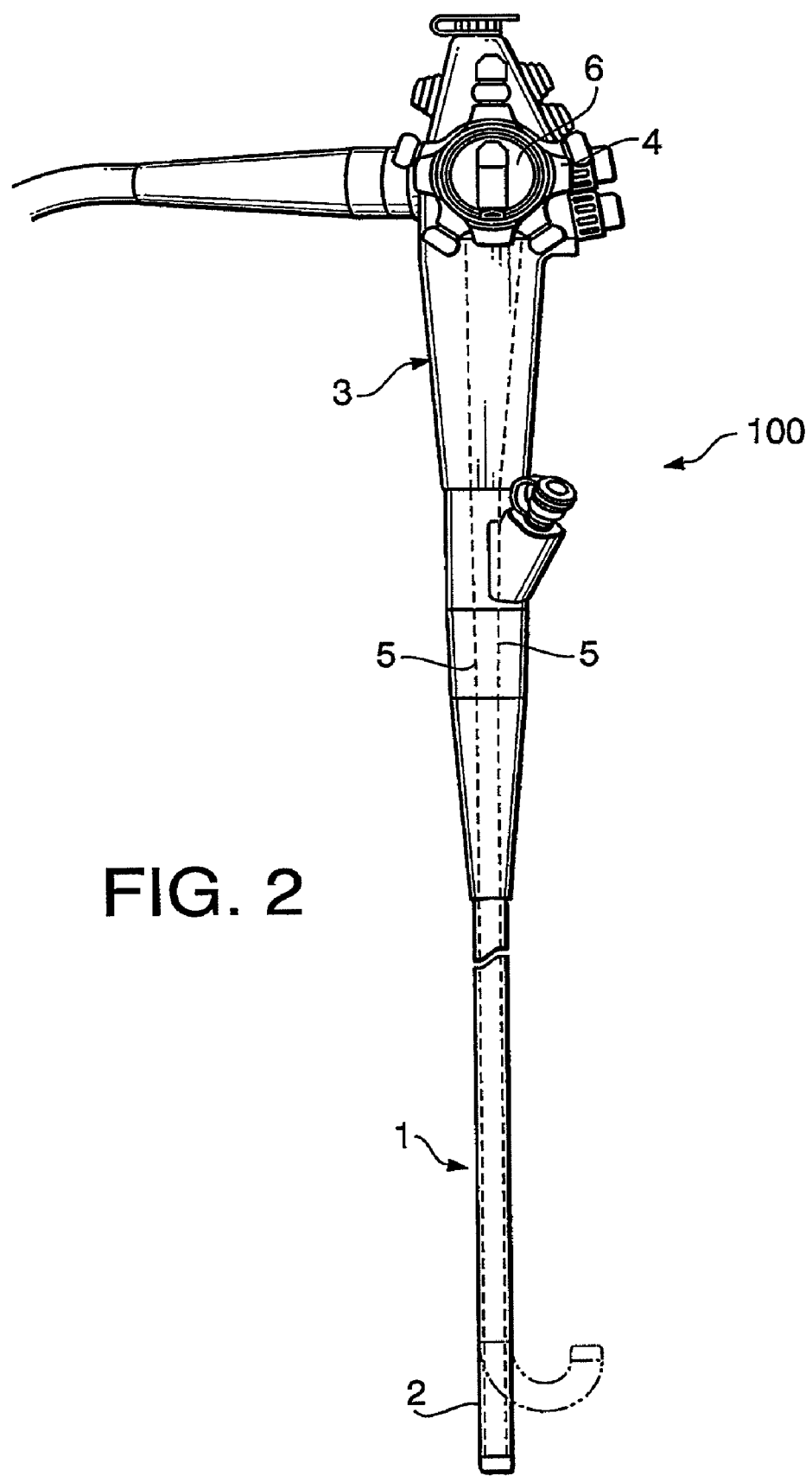
FIG. 2 is a side view of an endoscope employing the connection mechanism shown in FIG. 1.

FIG. 2 shows a side view of an endoscope 100 to which a connection mechanism according to the invention is applicable. The endoscope 100 has a flexible insertion section 1 and a distal end portion thereof is formed to be a bendable section 2. The bendable section 2 is driven by operation of an operation unit 3 connected to the proximal end of the insertion section 1.

Specifically, the operation unit 3 is provided with a bendable section operating knob 4 (hereinafter, simply referred to as a knob), which is rotatable with respect to the operation unit 3. By rotating the knob 4, one of a plurality of operating wires connected to the bendable section 2 is pulled, and the bendable section 2 is bent by an amount (i.e., angle) corresponding to the rotated amount of the knob 4. In FIG. 2, 6 denotes a bent state retaining knob to be used for retaining the bent state of the bendable section 2.

Figure 3:
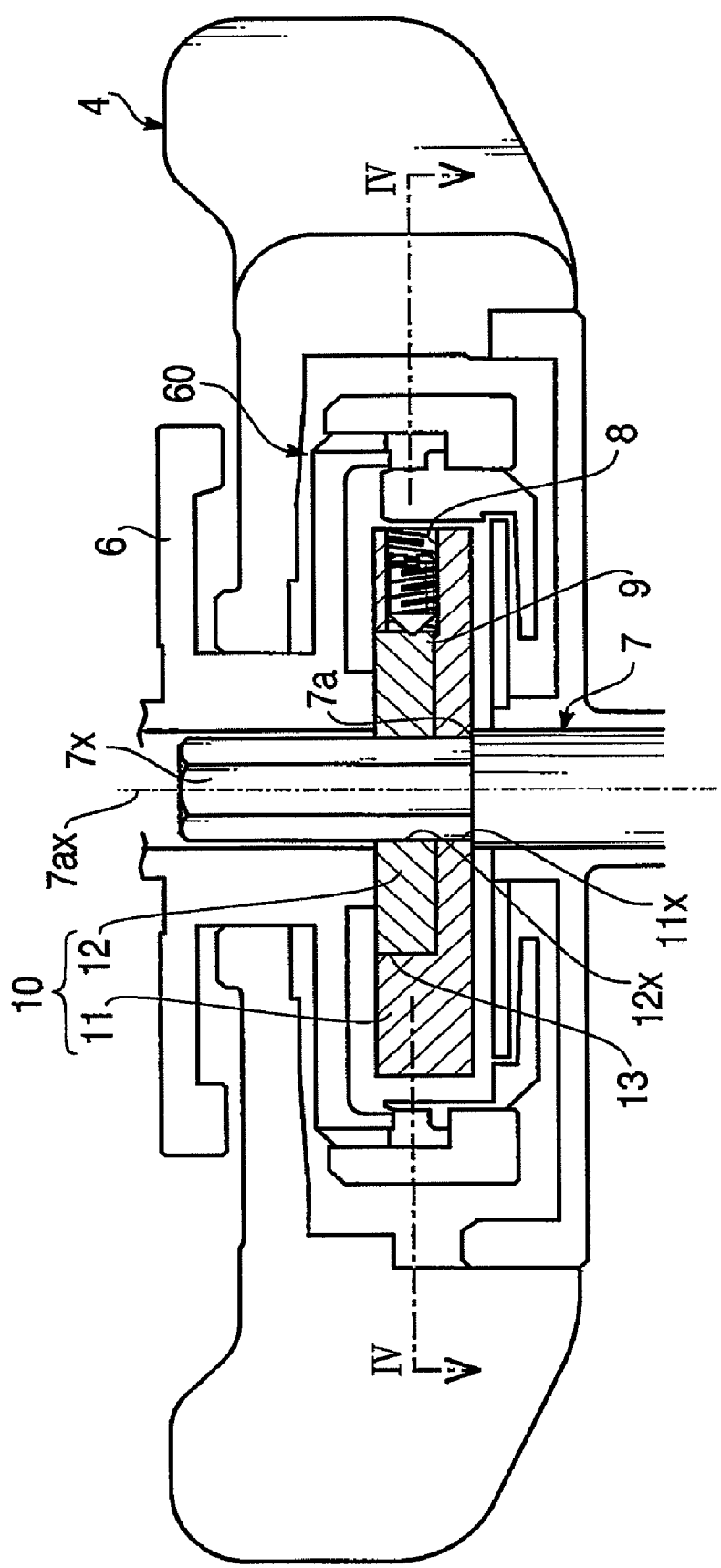
FIG. 3 is a cross-sectional side view of the connection mechanism according to the first embodiment.

FIG. 3 is a cross-sectional side view of the connection mechanism according to the first embodiment. In FIG. 3, 60 denotes a braking mechanism for applying frictional force for preventing the rotational movement of the knob 4 in accordance with the operation of the bent state retaining knob 6. The braking mechanism 60 is secured to a shaft member 7 which is fixedly secured onto the flame of the operation unit 3. A plate member 10 unrotatably connected to the shaft member 7 serves as a fixed member for braking operation.

It should be noted that the various braking mechanisms have been known, and since the present invention relates to a connection mechanism, which is a part of the braking mechanism and may be applied to other connecting mechanism, the operation of the braking mechanism 60 will not be described for brevity. An example of such a braking mechanism is disclosed in Japanese Patent Provisional Publication No. 2007-313292.

The shaft member 7 is provided with a polygonal column portion 7x. According to the first embodiment, a regular hexagonal column is employed. However, any other polygonal column may be used. The shaft member 7 has a cylindrical shape at portions other than the polygonal column portion 7x. At a boundary between the cylindrical portion and the polygonal portion 7x, as shown in FIG. 3, a step 7a is formed.

Figure 1:
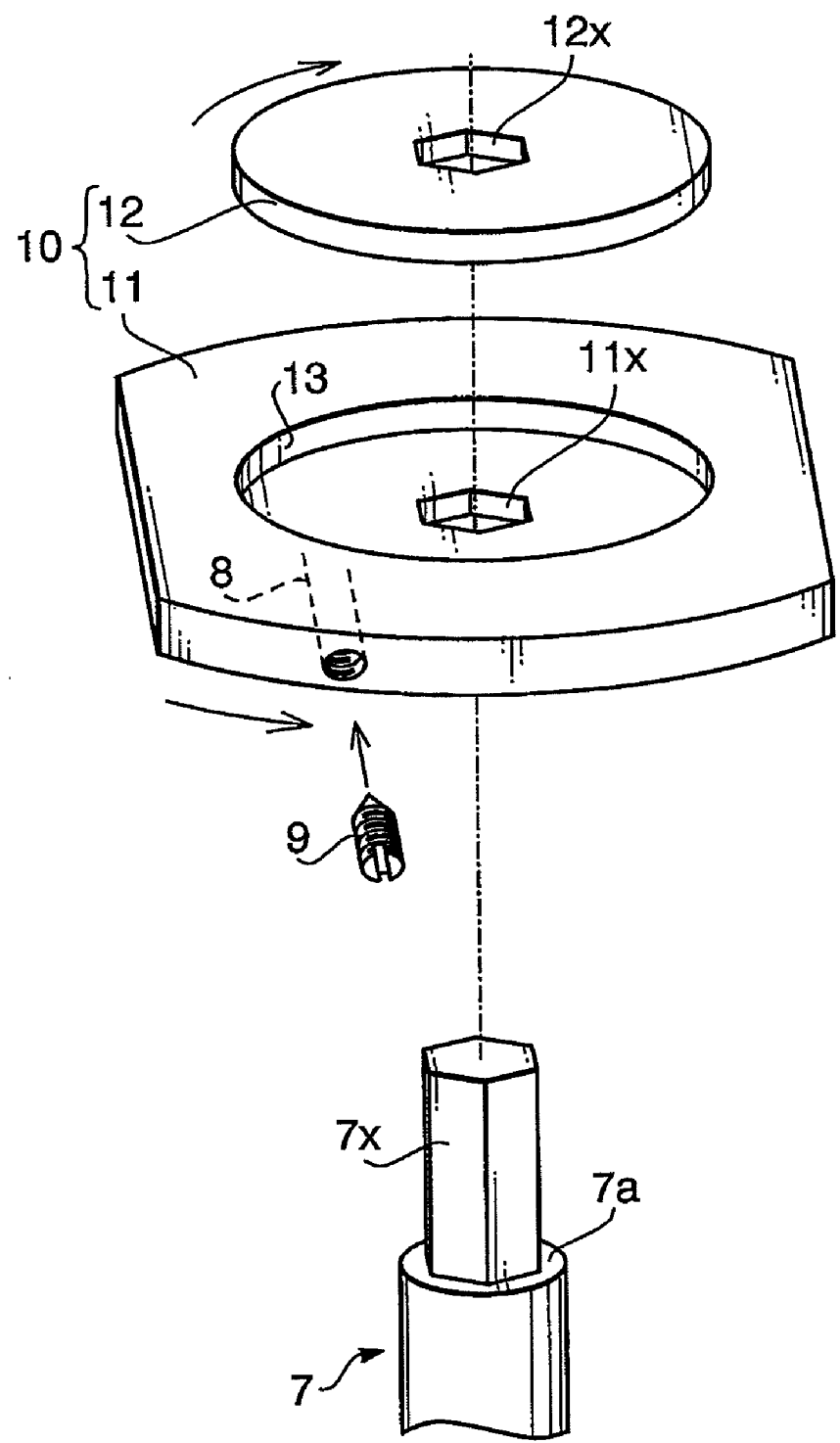
FIG. 1 is an exploded perspective view of a connection mechanism according to a first embodiment.
Figure 4:
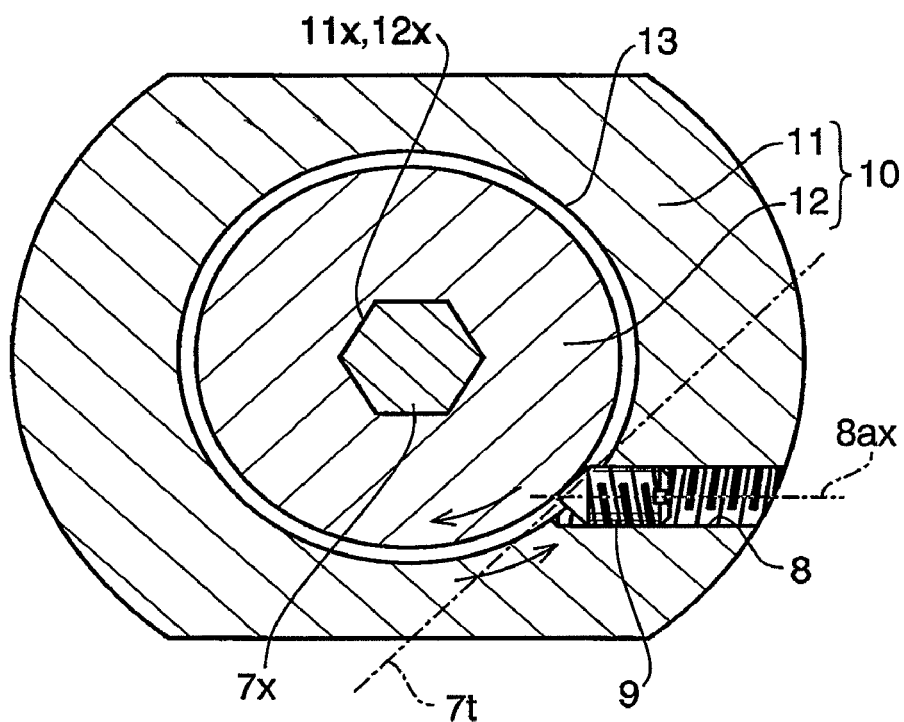
FIG. 4 is a cross-sectional plan view of the connection mechanism taken along line IV-IV in FIG. 3.

The plate member 10 includes first plate 11 and second plate 12, which are overlaid in the direction of the central axis 7ax of the shaft member 7 with each other, as shown in FIG. 4 showing a cross-sectional plan view of the connection mechanism taken along line IV-IV in FIG. 3, and FIG. 1 showing an exploded perspective view.

As clearly shown in FIG. 1, the second plate 12 has a disk-like member. On the first plate 11, a circular recess 13 is formed such that the second plate 12 is loosely fitted in the recess 13.

On the first plate 11 and second plate 12, polygonal (i.e., in the first embodiment, hexagonal) openings 11x and 12x to which the polygonal section 7x of the shaft member 7 tightly fitted in are formed, respectively.

As shown in FIG. 3, the first plate 11 is fitted on the polygonal section 7x such that the lower surface of the first plate 11 contacts the step 7a, and the second plate 12 is fitted on the polygonal section 7x and loosely fitted in the recess 13. With this structure, the plate member 10 does not rotate relative to the shaft member 7.

However, due to manufacturing errors, the size of the polygonal openings 11x and 12x may be not tightly fitted on the polygonal column section 7x, and play may remain in the rotational direction with respect to the central axis 7ax of the shaft 7.

As shown in FIG. 1 and FIG. 4, a screw hole 8 is formed on the first plate 11 such that a central axis 8ax of the screw hole 8 extends from an outer circumferential surface to the recess 13. As shown in FIG. 4, the direction where the screw hole 8 extends (i.e., the direction of the central axis 8ax of the screw hole 8) is inclined with respect to a tangential line 7t at which the central axis 8ax of the screw hole 8 intersects a circumferential surface of the second plate 12 (i.e., the screw hole 8 extends in a non-radial direction). Further, a screw 9 having a coned tip end is screwed in the screw hole 8 from the outer periphery of the first plate 11 toward the second plate 12.

By fastening the screw 9 tightly, the first plate 11 and the second plate 12 are urged to rotate in opposite directions as indicated by arrows in FIG. 4. Therefore, the polygonal opening 11x and polygonal opening 12x fasten the polygonal column section 7x in opposite directions. As a result, the plate member 10 is fixedly secured onto the polygonal column section 7x without any play at all in the rotational direction.

It should be noted that the present invention need not be limited to the above-described exemplary embodiment, and various modifications may be made without departing from the scope of the invention.

Figure 5:
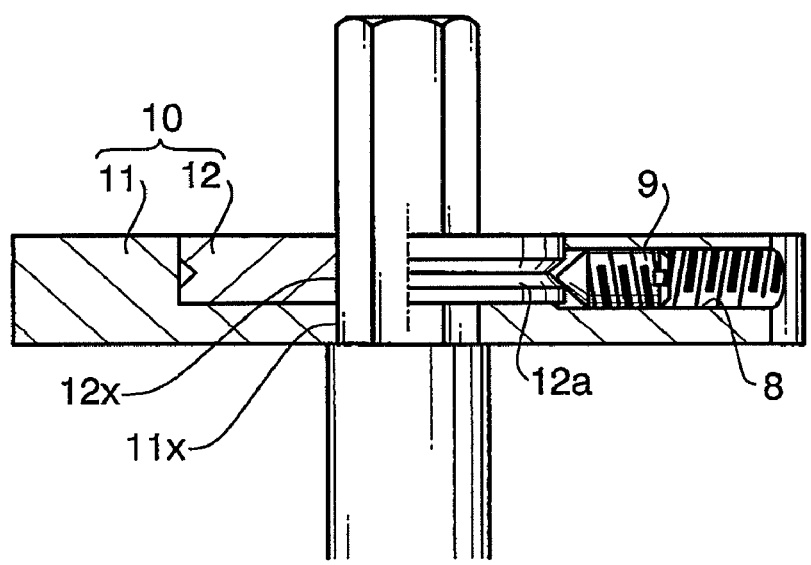
FIG. 5 is a cross-sectional side view of a connection mechanism according to a second embodiment.

FIG. 5 is a cross-sectional side view of a connection mechanism according to a second embodiment. According to the second embodiment, a groove 12a having a V-shaped cross section may be formed on the circumferential surface of the second plate 12 so that part of the pressing force of the screw 9 is converted to urge the second plate 12 toward the first plate 11.

Figure 6:
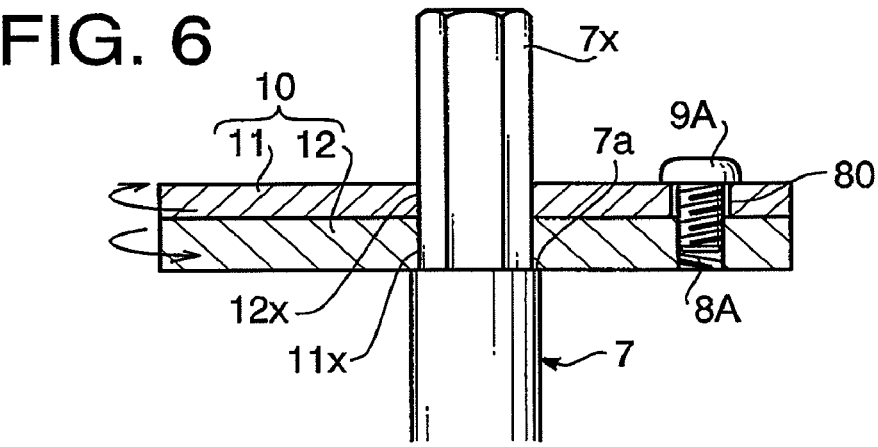
FIG. 6 is a cross-sectional side view of a connection mechanism according to a third embodiment.
Figure 7:
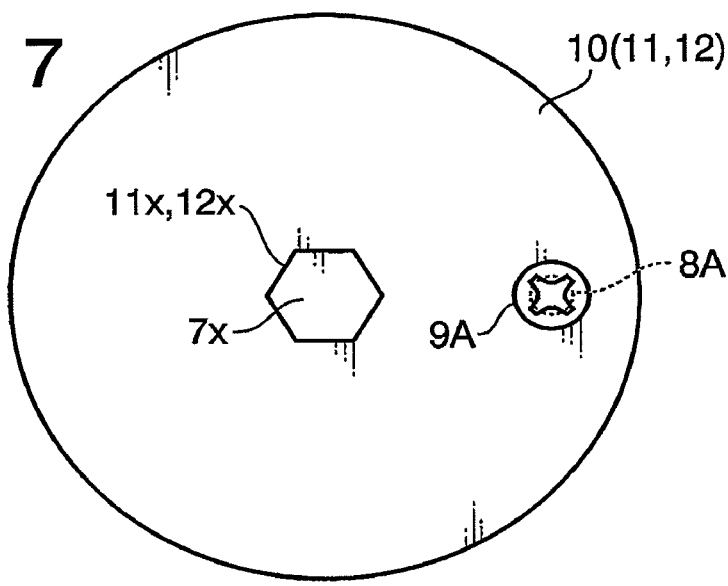
FIG. 7 is a plan view of the connection mechanism according to the third embodiment.

FIG. 6 is a cross-sectional side view of a connection mechanism according to a third embodiment, and FIG. 7 is a plan view of the connection mechanism according to the third embodiment. According to the third embodiment, a screw hole 8A is formed on the first plate 11 in the direction parallel to the central axis of the shaft 7, and a loose hole 80 allowing a screw 9A with play is formed on the second plate 12. According to the third embodiment, the user manually applies force to rotate the first plate 11 and the second plate 12 in opposite directions as indicated by arrows in FIG. 6, and with applying the urging force, the screw 9A is fastened tightly.

Figure 8:
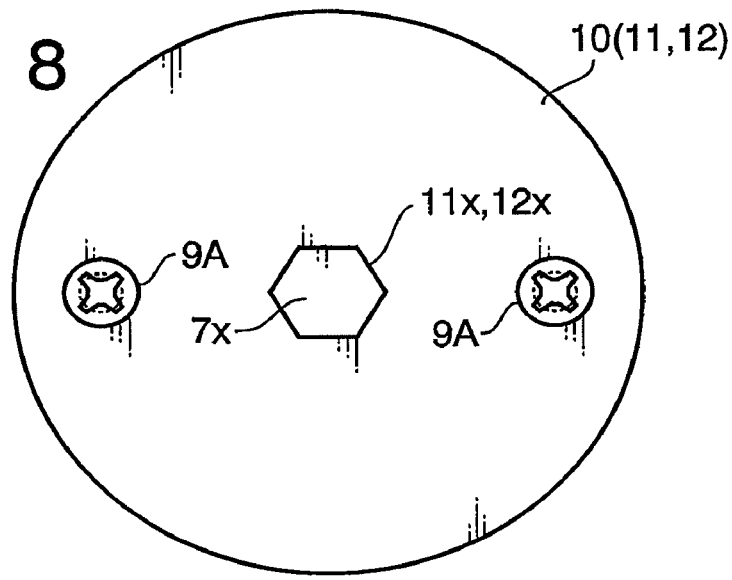
FIG. 8 is a plan view of a connection mechanism according to a fourth embodiment.
Figure 9:
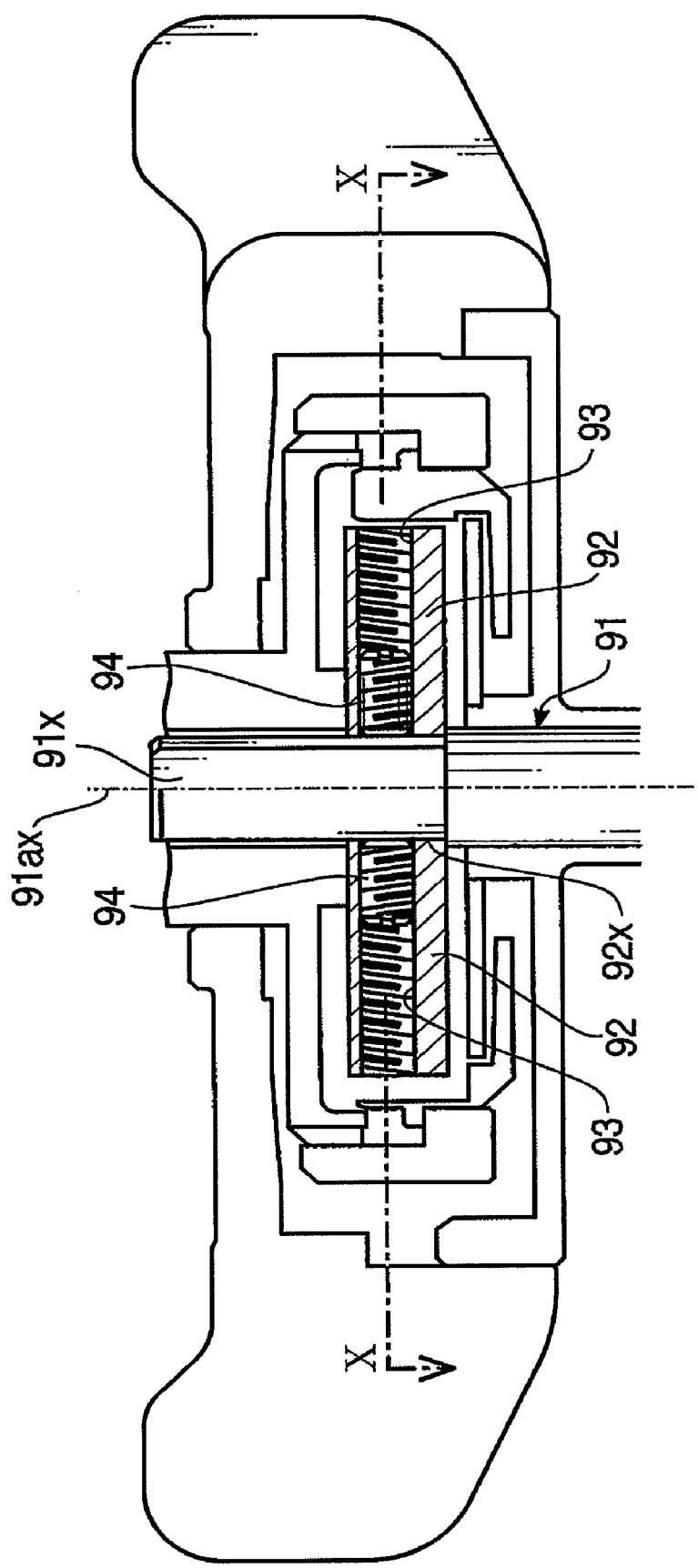
FIG. 9 is a cross-sectional side view of a conventional connection mechanism.
Figure 10:
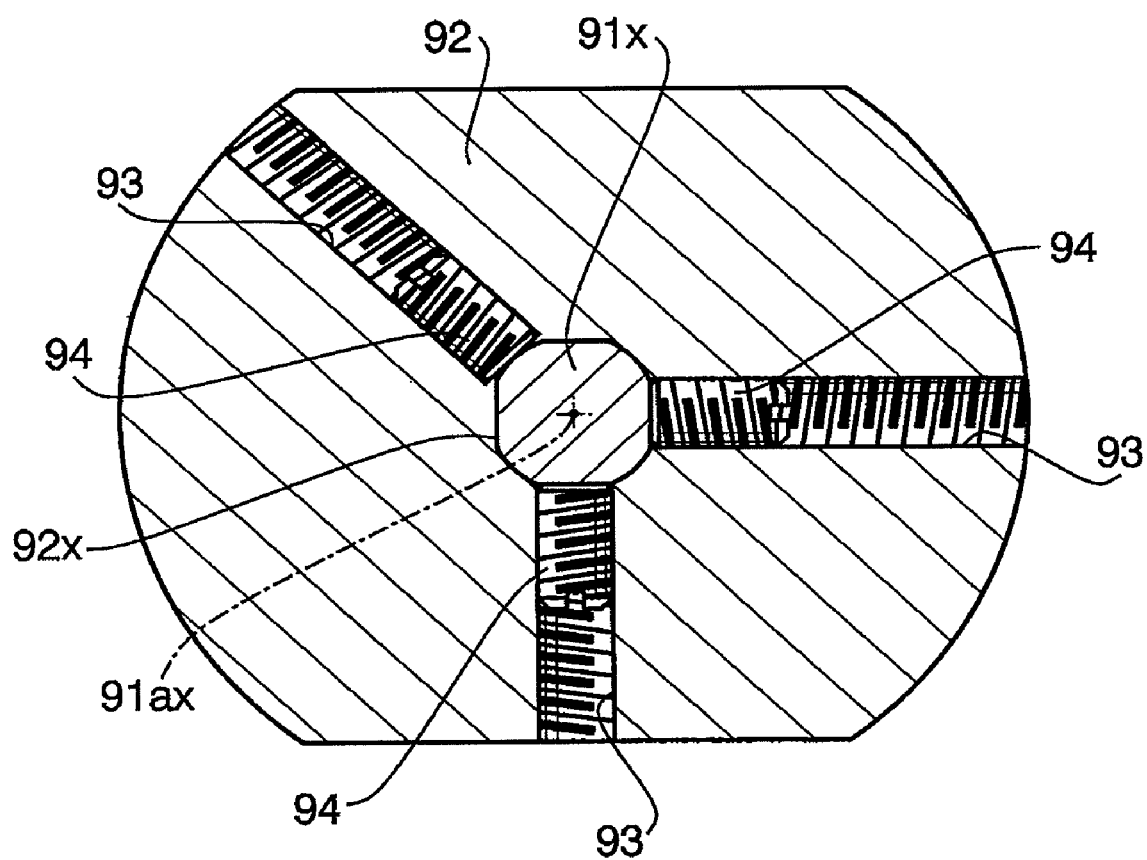
FIG. 10 is a cross-sectional plan view of the conventional connection mechanism taken along line X-X in FIG. 9.

FIG. 8 is a plan view of a connection mechanism according to a fourth embodiment. The fourth embodiment has a structure similar to the third embodiment except that a plurality of screws 9A (thus, a plurality of holes 8A) are used.

The present disclosure relates to the subject matter contained in Japanese Patent Application No. 2007-163337, filed on Jun. 21, 2007, which is expressly incorporated herein by reference in its entirety.

What is claimed is:

1. A connection mechanism for connecting an operation section of an endoscope, comprising:
   a plate member formed with a polygonal hole, the plate member including a first plate and a second plate overlaid with each other, each of the first plate and the second plate being formed with the polygonal hole;
   a shaft member formed with a polygonal column section fitted in the polygonal hole formed on the plate member; and
   a fixing mechanism that fixes the first plate and the second plate with each other to retain a status where the first plate and the second plate are urged oppositely in a rotational direction about a central axis of the shaft member, wherein
   the first plate is formed with a recess in which the second plate is fitted, wherein the second plate is formed with a V-shaped groove extending along a circumferential surface thereof, and wherein
   the fixing mechanism includes:
   a screw hole formed in the first plate extending from an outer periphery of the first plate to an outer periphery of the second plate fitted in the recess, the screw hole extending in a direction deflected from a direction toward the central axis of the shaft member; and
   a screw insertable in the screw hole, wherein when the screw is inserted in the screw hole, the screw urges the first plate and the second plate oppositely in the rotational direction about the central axis of the shaft member, and engages the V-shaped groove such that the second plate is urged towards the first plate along the direction of the central axis of the shaft member.

2. The connection mechanism according to claim 1, wherein the fixing mechanism includes:
   a screw hole formed in the first plate, the screw plate extending in a direction parallel to the central axis of the shaft member;
   a screw to be engaged with the screw hole; and
   a loose opening formed in the second plate for allowing the screw loosely fitted therein, the screw being fastened tightly with the first plate and the second plate being urged oppositely in the rotation direction about the central axis of the shaft member.

3. A connection mechanism for connecting an operation section of an endoscope, comprising:

a plate member formed with a polygonal hole, the plate member including a first plate and a second plate overlaid with each other, each of the first plate and the second plate being formed with the polygonal hole, and the second plate being formed with a V-shaped groove;

a shaft member formed with a polygonal column section fitted in the polygonal hole formed on the plate member; and a fixing mechanism that fixes the first plate and the second plate with each other to retain a status where the first plate and the second plate are urged oppositely in a rotational direction about a central axis of the shaft member, wherein the first plate is formed with a recess in which the second plate is fitted, and wherein the fixing mechanism includes:

a screw hole formed in the first plate extending from an outer periphery of the first plate to an outer periphery of the second plate fitted in the recess, the screw hole being offset from the shaft member and extending in a direction perpendicular to the central axis of the shaft member; and a screw inserted in the screw hole to engage the V-shaped groove, the screw urging the first plate and the second plate oppositely in the rotational direction about the central axis of the shaft member.

* * * * *